(12) United States Patent
Paldus et al.

(10) Patent No.: US 7,154,595 B2
(45) Date of Patent: Dec. 26, 2006

(54) CAVITY ENHANCED OPTICAL DETECTOR

(75) Inventors: Barbara Paldus, Sunnyvale, CA (US); Alexander Katchanov, Sunnyvale, CA (US); Robert Provencal, San Jose, CA (US)

(73) Assignee: Picarro, Inc., Sunnyvale, CA (US)

( * ) Notice: Subject to any disclaimer, the term of this patent is extended or adjusted under 35 U.S.C. 154(b) by 342 days.

(21) Appl. No.: 10/738,599

(22) Filed: Dec. 17, 2003

(65) Prior Publication Data

US 2005/0134836 A1    Jun. 23, 2005

(51) Int. Cl.
*G01N 21/00* (2006.01)
(52) U.S. Cl. ...................................................... 356/73
(58) Field of Classification Search ............ None
See application file for complete search history.

(56) References Cited

U.S. PATENT DOCUMENTS

| | | | | |
|---|---|---|---|---|
| 5,022,033 | A * | 6/1991 | Hackell ....................... | 372/25 |
| 6,839,140 | B1 * | 1/2005 | O'Keefe et al. ............. | 356/436 |
| 2003/0109055 | A1 * | 6/2003 | Lehmann et al. ............ | 436/164 |
| 2003/0210398 | A1 * | 11/2003 | Augustine et al. .......... | 356/432 |
| 2004/0061859 | A1 * | 4/2004 | Taubman ..................... | 356/437 |
| 2004/0207852 | A1 * | 10/2004 | Bechtel et al. .............. | 356/440 |

* cited by examiner

*Primary Examiner*—Michael P. Stafira (57) ABSTRACT

A cavity enhanced optical detector comprising: i) a source of continuous wave laser light; ii) a high finesse resonant cavity comprising at least three spaced apart, high-reflectivity mirrors positioned to receive light from the laser light source; iii) at least one photo-detector for measuring the extinction coefficient of an analyte that is positioned in the resonant cavity; and iv) one or more additional photo-detectors for measuring the intensity of fluorescence emission and/or Raman scattering from the analyte.

20 Claims, 7 Drawing Sheets

5.1-Ringdown Mirror 5.2-Forward/Back Scattering Collection Lenses 5.3-Fluorescence or Scattering Collection Lenses 5.4-Ringdown Beam Path

Brewster Cell in Cavity

CAVITY ENHANCED OPTICAL DETECTOR

FIELD OF THE INVENTION

This invention relates to a cavity enhanced optical detector which is able to substantially simultaneously measure extinction coefficient, scattering and fluorescence and/or Raman scattering of gaseous aerosols.

BACKGROUND OF THE INVENTION

The presence of various types of contaminants in the earth's atmosphere or in the internal atmosphere of a work place or other structure is a matter of world-wide concern. A great variety of adverse effects including global warming, transmission of contagious diseases and numerous long term health problems such as emphysema have been attributed to a wide variety of atmospheric contaminants. Atmospheric contaminants can be broadly divided into three categories based on their physical form, i.e., solid, liquid, or gaseous and then in some of these cases further subdivided into organic, inorganic and biological. For example, harmful inorganic vapors present in the atmosphere include $SO_2$, nitrogen oxides and mercury. Inorganic solid contaminants include cement dust and ammonium sulfate. Examples of organic vapors include chlorofluorocarbons and various aromatic hydrocarbons. Particularly at lower temperatures, many even relatively low molecular weight organic compounds can be present in the atmosphere in liquid or even solid particulate form. Of particular concern are atmospheric liquid and solid biological materials ("bioaerosols")

The Bioaerosol Problem

Bioaerosols are airborne particles consisting of, or derived from living organisms such as e.g., bacteria, viruses, molds, fungi, pollens, dust mites insect remains and pet dander. They have both natural and anthropogenic sources and are ubiquitous in the earth's tropospheric boundary layer. Bioaerosols are found, for example, in the workplace, in houses, in medical facilities, in manufacturing operations, in dairy or other animal housing facilities, in sites of sludge application, in recycling and composting plants, in sanitary landfills, and in sewage plants. Unlike most common non-biological origin atmospheric aerosols, airborne bioaerosols can cause immediate disease, allergic reactions and/or respiratory problems. Bioaerosols are also particularly feared as potential biowarfare and terrorist agents.

Current methods that measure aerosol particle size distribution in real time provide insufficient information about particle types (i.e., inorganic vs. organic vs. biological) and are not able to identify specific microorganisms. Although efforts to develop field useable instruments for the detection and identification of airborne biological particles have accelerated during the last several years, improved methods for characterizing all types of aerosols, particularly bioaerosols, are urgently needed. There is a need to quantify airborne microorganisms for among other things: (i) the biotechnology industry, (ii) the evaluation of indoor and outdoor air quality, (iii) investigations of infectious disease outbreaks, and (iv) agricultural health investigations. Today, there is a major technological void in bioaerosol sampling techniques. To determine the sources and effects of bioaerosols on human and animal health, a need exists for an instrument that is capable of accurately and reliably measuring aerosol optical properties while simultaneously discriminating between biological and non-biological aerosols.

Biowarfare and Bioterrorism

Bioaerosols represent a particularly dangerous class of biological weapons. As such, methods of detecting and characterizing bioaerosols are greatly needed. As already indicated, there currently does not exist any accurate real-time method for the detection and identification of atmospheric and/or indoor air biological particles. Present real-time aerosol detection methods provide only a general indication of size-distribution and provide virtually no information on particle type.

Considering the enormous threat posed by bioaerosols to the population at large, fieldable methods for detecting and characterizing these hazards are urgently needed. Instruments that operate in the field must be able to withstand mechanical vibration and shock, produce accurate and reliable results without the need for manual calibration or expert attendance, and preferably operate without consumables.

Aerosols and Climate Change

In recent decades global warming has taken terrestrial temperatures to their highest levels in at least the past millennium. While the causes of global warming continue to be debated, there is considerable evidence that atmospheric aerosols play an important role. Because most aerosols reflect sunlight back into space, they also have a "direct" cooling effect by reducing the amount of solar radiation that reaches the surface of the Earth. The magnitude of this reverse radiation (known as "radioactive forcing") depends on the size and composition of the aerosol particles, as well as their optical properties. It is thought that aerosol cooling may at least partially offset the expected global warming that is attributed to increases in the amount of atmospheric carbon dioxide resulting from human activity. The size of these various effects, is, however, not well understood, mainly due to the lack of accurate optical data. An International Panel on Climate Change has identified radiative forcing due to the presence of aerosols as one of the most uncertain components of climate change models and as a topic urgently in need of further research.

There is therefore a pressing need for an analytical instrument having the following capabilities: i) the ability to substantially simultaneously detect the presence in the atmosphere of inorganic, organic and bioaerosols; and ii) distinguish bioaerosols from non-biological particulates and dispersed liquids (organic and/or inorganic) and also to identify certain specific bioaerosols. To accomplish these multiple tasks the instrument should be able to do the following: 1) perform extinction and Rayleigh scattering measurements to estimate the quantity and size distribution of liquid and solid particles (i.e., inorganic, organic and biological) present in the atmospheric sample: and 2) measure laser induced fluorescence and/or Raman scattering of bioaerosols to facilitate identification. It should be noted that although fluorescence can be induced in certain organic compounds, such fluorescence is normally much weaker than that of biological compounds and also the fluorescence spectra of organic and biological materials are significantly different. The difference between the quantity of aerosol indicated by procedures 1 and 2 is therefore also a measure of the inorganic and organic (non-biological) liquid and solid atmospheric contaminants. Accuracy is, of course, enhanced if measurements 1 and 2 are performed substantially simultaneously. In addition, if possible, the instrument should be able to perform Rayleigh scattering and fluorescence at several wavelengths to permit estimation of particle size distribution. Likewise, the Raman spectrum of many compounds are unique and frequently specific organic or biological components can be detected by analyzing the Raman scattering of complex mixtures including aerosols. The distinction between Raman scattering and Rayleigh scattering is that the latter is at the same wavelength as the incident radiation while Raman scattering is at a longer wavelength (Stokes) or higher frequency (anti-Stokes). A reference to "scattering" herein, without further qualification, is to be construed as Rayleigh scattering.

Designing an instrument that can accurately and rapidly perform these multiple measurements is technically challenging. In particular, building an apparatus that exploits the intrinsic fluorescence and/or Raman emissions of bioaerosol particles for their detection and classification is challenging for several reasons. First, the particles of interest may be present in very low concentration in a dominant background. Average fluorescence or Raman spectra accumulated for a population of aerosol particles will frequently yield little or no information about the few particles of specific interest, i.e., single-particle spectra are required. Second, fluorescence signals are generally weak because individual particles generally contain only a few picograms of material. Additionally, only a small fraction of the mass of most biological particles consists of fluorophores. Likewise, Raman scattering by its nature is weaker than the illuminating radiation. Third, particles are generally dispersed non-uniformly in the air (their concentration fluctuations follow the Kolmogorov spectrum of atmospheric turbulence), and they must be detected at random times as they are carried by a stream of air through an optical cell. Fourth, an optimal detector must be able to excite particles in the ultraviolet where most biological molecules (and hence biological particles) fluoresce to a significant extent. Ultraviolet laser sources are generally costly and have a relatively low energy output. In many environments the dominant background particles are nonbiological so that a minority concentration of bioaerosols must be differentiated from these nonbiological particles. However, because the UV-excited fluorescence is typically weaker from non-biological as compared to biological particles, the un-dispersed fluorescence intensity can be used to differentiate between these two types of particles. In the case of Raman spectroscopy, most biological particles show their strongest emission when excited by radiation in the visible and near UV region (100–700 nm), so an optimal detection instrument must be able to provide incident radiation in this wavelength range.

We have developed an instrument using the principles of cavity enhanced optical detection which is capable of performing the above-indicated multiple measurements i.e., extinction coefficient, scattering and fluorescence and/or Raman scattering. In addition, our preferred instrument is uniquely compact and portable, and has low power consumption. These features are highly advantageous since much monitoring of atmospheric pollutants must take place by aircraft at altitudes of up to 50,000 feet.

The operation of our instrument, which is also readily integrated into an indoor air quality monitoring system, involves the following steps:

1) Determine the extinction coefficient by measuring the ring down time using filtered air (i.e., an atmospheric sample free from any liquid or solid particles). This will provide the "background" extinction coefficient of the instrument (i.e., any absorption due solely to gases present in the air and also any scattering or absorption due to the instrument mirrors and intra-cavity interfaces).

2) Measure the extinction coefficient of the aerosol containing (unfiltered) atmospheric sample. The difference between results 1 and 2 provides the extinction due to the aerosols present in the sample. Although not essential, simultaneous measurement of scattering and extinction provides enhanced accuracy.

3) Measure scattering since extinction minus scattering equals the absorption by the liquid and/or solid aerosol particles.

4) Measure scattering simultaneously at several different wavelengths. This provides particle size information since scattering is a function of particle size and is proportional to $1/\lambda^4$ 5) Obtain the fluorescent and/or Raman spectra to permit differentiation between biological and non-biological samples. Since the strength of the fluorescence of biological particles is significantly greater than that of organic and inorganic particles, by appropriate choice of the incident laser wavelength (near UV of 100 to 400 nm, or visible 400–700 nm, is particularly suitable) one can virtually eliminate any significant fluorescence by the non-biological constituents of the sample. In addition, a plot of the fluorescence spectra permits identification of certain bioaerosol components. For Raman detection incident radiation in the 400 to 700 nm range (visible) is especially suitable.

As previously indicated, the extinction coefficient of the aerosol containing sample is a measure of the combined effects of scattering by the cavity mirrors and the liquid and solid particulate content of the sample plus absorption by the solid, liquid and gaseous sample components. If scattering by the sample alone is then determined, the difference between extinction and scattering is equal to absorption by the aerosol constituents present. Finally, fluorescence or Raman measurement permits estimation of the biological component of the total liquid and solid particulates, which can frequently be identified by their Raman spectrum.

Optical detection is the determination of the presence and/or concentration of one or more target species present in a sample by illuminating the sample with optical radiation and measuring optical absorption, induced fluorescence, and/or optical scattering by the sample. Optical detection has a wide variety of applications, and a correspondingly wide variety of optical detection methods are known. Cavity enhanced optical detection entails the use of a passive optical resonator, also referred to as a cavity, to improve the performance of an optical detector. Cavity enhanced absorption spectroscopy (CEAS), sometimes called integrated cavity output spectroscopy (ICOS), and cavity ring down spectroscopy (CRDS) comprise the most widely used cavity enhanced optical detection technology. Cavity enhanced optical detection, either CEAS or CRDS can be used for solid, liquid, aerosol, or gaseous samples.

The intensity of single-mode radiation trapped within a passive optical resonator decays exponentially over time, with a time constant $\tau$, which is often referred to as the ring-down time. In practice, it is desirable to ensure that only a single resonator mode has an appreciable amplitude, since excitation of multiple resonator modes leads to multi-exponential radiation intensity decay (i.e., multiple time constants), which significantly complicates the interpretation of measurement results. The ring-down time $\tau$ depends on the cavity round trip length and on the total round-trip optical loss within the cavity, including loss due to absorption and/or scattering by one or more target species within a sample positioned inside the cavity. Thus, measurement of the ring-down time of an optical resonator containing a target species provides spectroscopic information on the target species. Both CRDS and CEAS are based on such a measurement of $\tau$.

In CRDS, an optical source is usually coupled to the resonator in a mode-matched manner, so that the radiation trapped within the resonator is substantially in a single spatial mode. The coupling between the source and the resonator is then interrupted (e.g., by blocking the source radiation, or by altering the spectral overlap between the source radiation and the excited resonator mode). A detector typically is positioned to receive a portion of the radiation leaking from the resonator, which decays in time exponentially with a time constant $\tau$. The time-dependent signal from this detector is processed to determine $\tau$ (e.g., by sampling the detector signal and applying a suitable curve-fitting method to a decaying portion of the sampled signal).

Single spatial mode excitation of the resonator is also usually employed in CEAS, (sometimes called integrated cavity output spectroscopy (ICOS)), but CEAS differs from CRDS in that the wavelength of the source is swept (i.e., varied over time), so that the source wavelength coincides briefly with the resonant wavelengths of a succession of resonator modes. A detector is positioned to receive radiation leaking from the resonator, and the signal from the detector is integrated for a time comparable to the time it takes the source wavelength to scan across a sample resonator mode of interest. The resulting detector signal is proportional to $\tau$, so the variation of this signal with source wavelength provides spectral information on the sample. Note that CEAS entails a relative measurement of $\tau$.

In cavity enhanced optical detection, the measured ringdown time depends on the total round trip loss within the optical resonator. Absorption and/or scattering by target species within the cavity normally accounts for the major portion of the total round trip loss, while parasitic loss (e.g., mirror losses and reflections from intracavity interfaces) accounts for the remainder of the total round trip loss. The sensitivity of cavity enhanced optical detection improves as the parasitic loss is decreased, since the total round trip loss depends more sensitively on the target species concentration as the parasitic loss is decreased. Accordingly, both the use of mirrors with very low loss (i.e., a reflectivity greater than 99.99 percent), and the minimization of intracavity interface reflections are important for cavity enhanced optical detection.

Several recently published treatises, including the references cited therein, cover most currently reported aspects of CRDS and CEAS technology: "Cavity-Ringdown Spectroscopy" by K. W. Busch and M. A. Busch, ACS Symposium Series No. 720, 1999 ISBN 0-8426-3600-3 and "Cavity Enhanced Spectroscopy" R. Peeters, Katholieke Univeristeit Nijmegen, The Netherlands, 2001, ISBN 90-9017628-8. CEAS is also discussed in a recent article entitled "Incoherent Broad-band Cavity-enhanced Absorption Spectroscopy" by S. Fiedler, A. Hese and A, Ruth Chemical Physics Letters 371 (2003) 284–294. However, none of these references teaches the simultaneous measurement of Rayleigh scattering, extinction coefficient and fluorescence and/or Raman scattering.

BRIEF DESCRIPTION OF THE DRAWINGS

FIG. 1 is a schematic of a two mirror (numbered 1 and 2) CRDS system. In the basic CRDS technique, a laser beam is injected into an optical cavity formed by two (or more) high-reflectivity mirrors, filling it with photons. The photons bounce back and forth between the mirrors up to 15,000 times. Most of them stay within the cavity for about 10 microseconds, traveling several kilometers during this time. In each round trip, about 0.01% of the photons pass through mirror 2 and strike a photo-detector 3. At a time $t_0$ the laser beam shuts off, and all the photons escape from the cavity over the next few microseconds.

This mathematical relationship holds not only for the light circulating within the cavity, but also for the light escaping from the cavity, since these two quantities are related by the transmissivity of the mirror 2, which is a constant. The light escaping from the cavity strikes the photodetector 3, which responds with a voltage proportional to the intensity of the incident light. The voltage across the detector as shown in FIG. 1 therefore decays exponentially starting at $t_0$, when the laser beam shuts off. The voltage across the photodetector at time t equals the voltage across the photodetector at $t_0$ multiplied by e to the $-t/\tau$.

The fundamental principles of operation of our CRDS (or CEAS) instrument are the same as for a two mirror cavity, The laser light is allowed to build up in the resonator, and when it reaches a threshold, it is shut off (e.g., with an external modulator). This trigger initiates the acquisition of the ring-down decay constant as well as the measurement of scatter, which will also exponentially decay as the intracavity intensity exponentially decays. By using multiple laser input wavelengths, scattering and fluorescence at multiple wavelengths can be detected simultaneously. One can detect the fluorescence intensity or integrated fluorescence signal which will behave similarly to the scattering signal but will, of course, be at a wavelength longer than the original laser excitation wavelength.

The presence of aerosol particles will increase the cavity's decay rate, due to both scattering and absorption by the particles. By measuring the decay rate of the cavity, a CRDS or CEAS instrument can determine the extinction coefficient of the aerosol containing sample gas with extreme sensitivity. Moreover, high optical intensities build up within the ringdown cavity. This enhances the intensity of both the scattering (Rayleigh and Raman) and fluorescence signals from aerosols. If one uses a linear cavity as shown in FIG. 1, the intracavity power circulates in both directions along the cavity axis thereby forming a standing wave. This wave can have maxima and minima where scattering is maximized or minimized, leading to a periodic variation of the scattering signal along the cavity especially for relatively small particles (e.g., 0.1 um particle vs. 1.5 um light). Also this changes the complexity of the actual scattering profile in that a single particle can scatter light in both directions, which can confound the scattering signatures from asymmetric particles. In a ring cavity, the intracavity light is a traveling wave which is unidirectional (i.e., circulates in one direction only, as shown in FIG. 3) and thus does not have modes and antinodes. This simplifies the scattering profiles. However, not all ring resonator designs are equal. For example, the sample volume is preferably minimized in order to enhance the response time of the detector. Also, there must be enough space between the beam paths of the ring resonator for the sample to only "see" one arm of the resonator (i.e., a traveling wave going in only one direction).

This is sometimes difficult to achieve with a triangular resonator, and a square resonator creates a large footprint. Therefore, although a three mirror ring, or four mirror rectangular (including square) cavity can be used to practice the invention, our preferred cavity configuration is a "bow-tie" shape as shown in FIGS. 3–6.

DETAILED DESCRIPTION OF THE DRAWINGS

Examples of CRDS instruments or portions thereof in accordance with the present invention are shown in FIGS. 3–8. Note that essentially the same configuration is equally applicable to a CEAS instrument.

Figure 1:
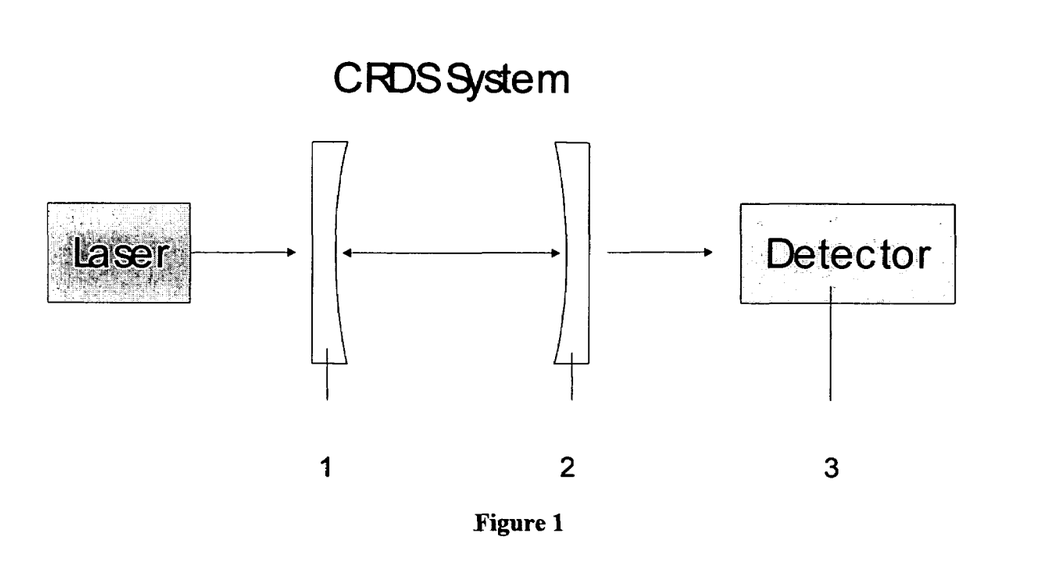
Figure 2:
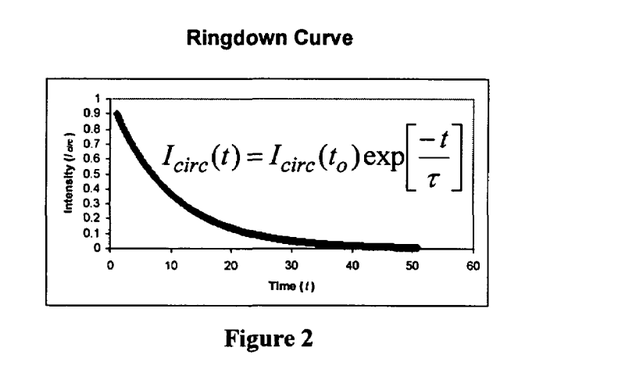
FIG. 2 shows a typical ringdown curve, which plots the intensity of light inside the cavity as a function of time (in microseconds) after the laser shuts off. The intensity of light inside the cavity decreases exponentially with a time constant $\tau$ (normally about 10 microseconds), the time interval over which the intensity of light diminishes by 1/e. The equation set forth within FIG. 2 above indicates that the intensity of light ($I_{circ}$) circulating inside the cavity at any given moment equals the intensity of light which was circulating in the cavity at $t_0$, when the laser beam shut off, multiplied by e to the $-t/\tau$.
Figure 3:
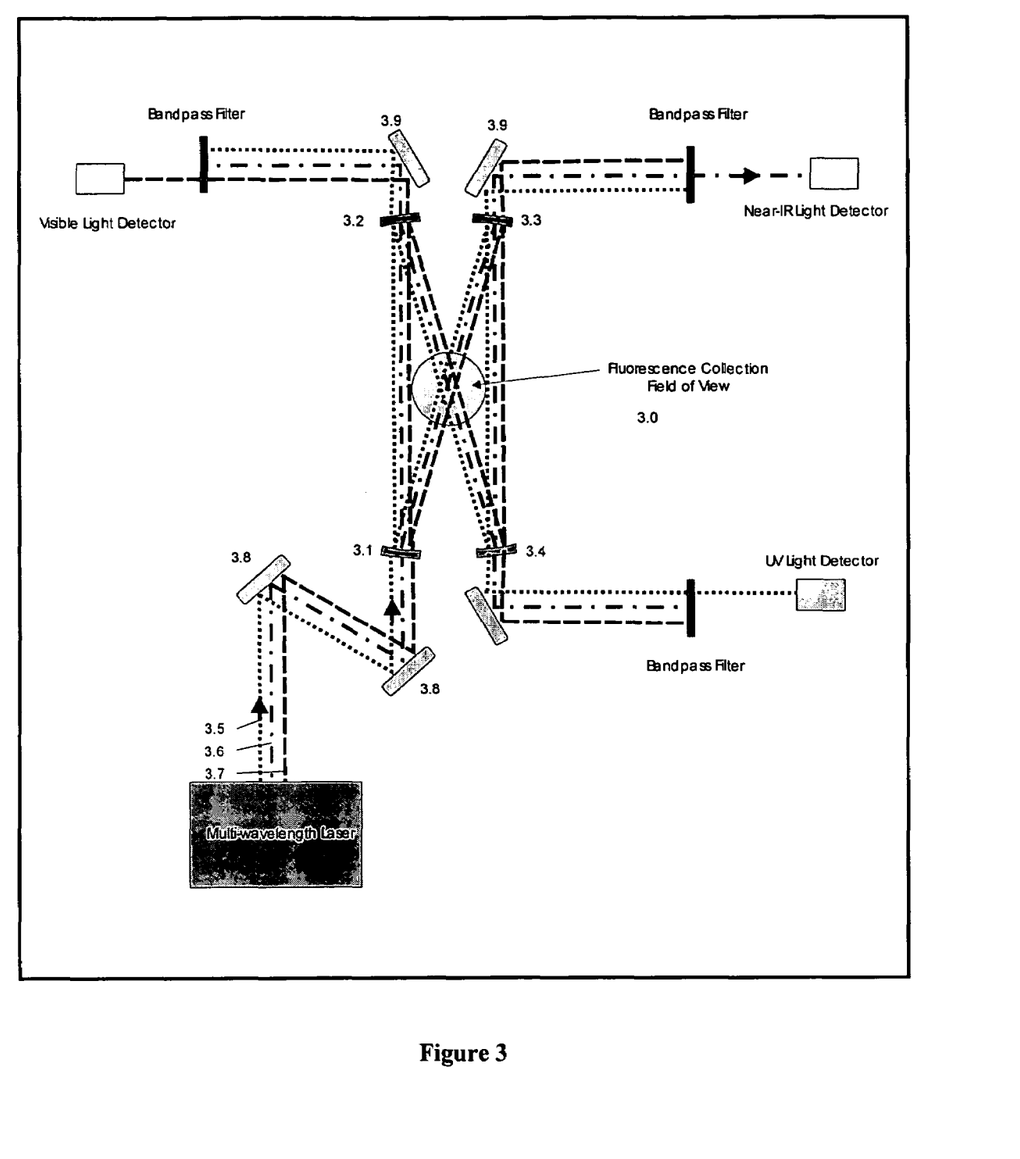
FIG. 3 is a schematic top view of a CRDS instrument according to the present invention utilizing a single multi-wavelength (frequency doubled) laser.
Figure 4:
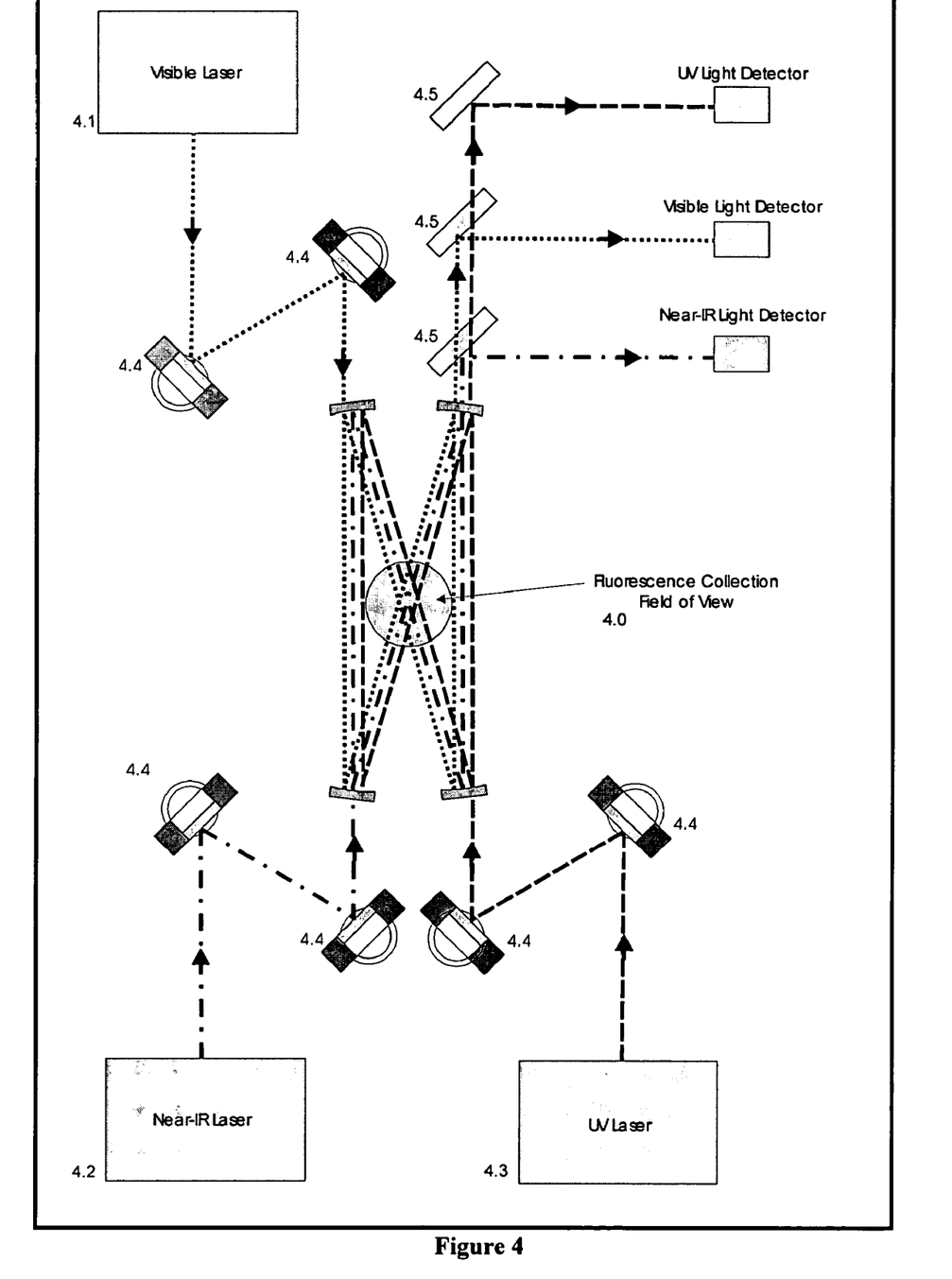
FIG. 4 is a schematic top view of a CRDS instrument according to the present invention using three different lasers each of a different wavelength.
Figure 5:
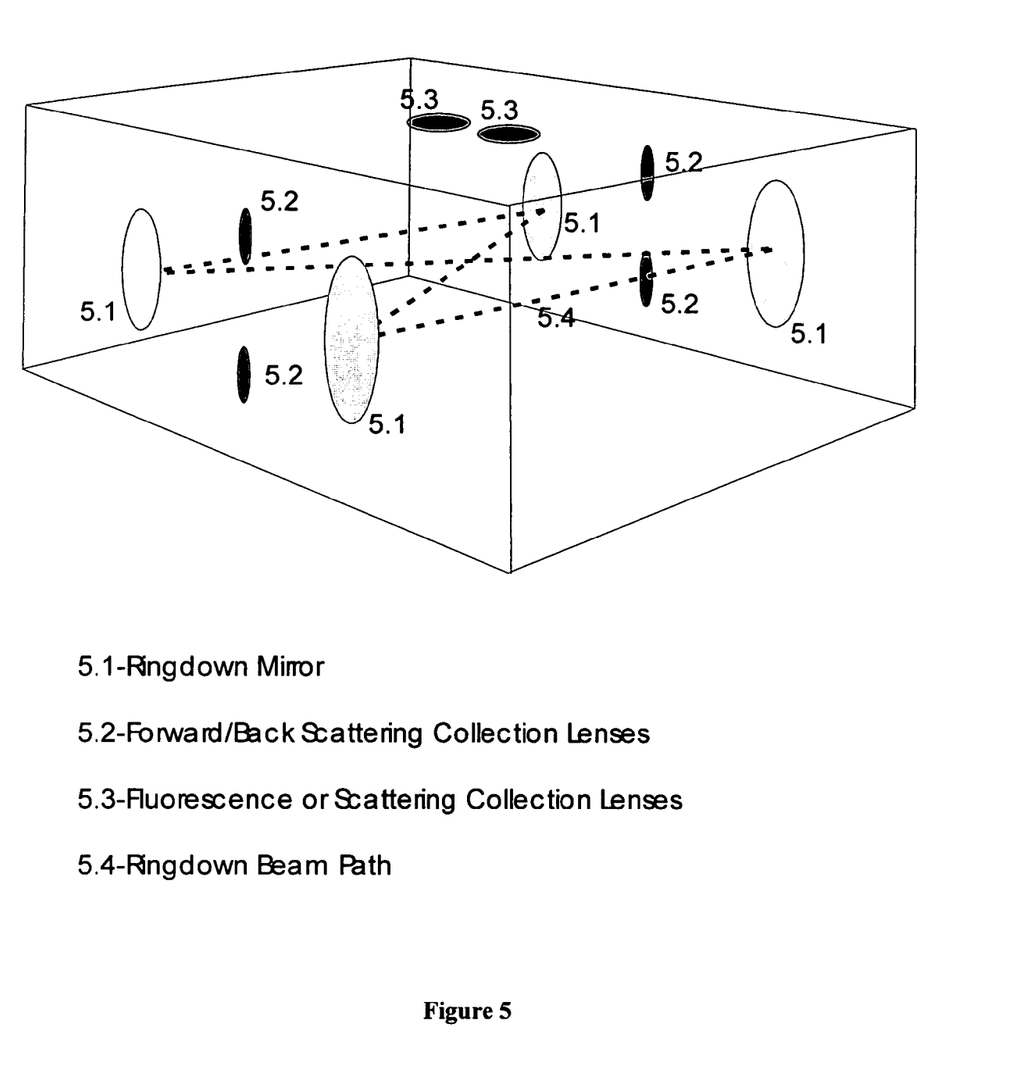
FIG. 5 is a three dimensional schematic of a portion of a CRDS instrument according to the present invention showing the ringdown mirrors, beam path and fluorescence and scattering collection lenses.

Although a three mirror triangular or four mirror rectangular cavity can be utilized, our instrument preferably has a unique four mirror "bow-tie" cavity configuration as shown in FIGS. 3–6. The cavity consists of a high finesse resonator using four mirrors (preferably plano-concave) shown as 3.1, 3.2, 3.3 and 3.4. This configuration has several unexpected advantages, as compared with conventional two- and three-mirror designs, including: (i) simplified alignment, (ii) longer optical interaction length, (iii) uniformity of mirror optics; and (iv) simplified coupling of multiple laser wavelengths into the cavity since when using multiple lasers (as shown in FIG. 4) each wavelength can have its own input coupling mirror. In addition, the bowtie configuration increases the effective cavity path length, as compared to a similar size linear cavity. As shown in FIG. 3, the laser beams 3.5, 3.6 and 3.7 strike all four mirrors, making two passes through the cavity, i.e., four passes for one round-trip. When using all plano-concave mirrors, all four mirrors can be identical and can, therefore, be fabricated in a single coating run. The cost of a mirror coating run is high, so this simplification in mirror optics significantly reduces the CRDS system cost. As an alternative to four plano-concave mirrors, one can use two flat and two plano-concave mirrors. Again, although the mirror substrates would not all be identical, a single coating run could be carried out. In addition, if the input laser(s) do(es) not vary in frequency, only one of the mirrors, e.g., 3.1 in FIG. 3, of the cavity needs to be dithered to provide a resonant cavity. Alternatively, one can utilize a fixed cavity and dither the laser. By using a high finesse, optical build-up ring down cavity as shown, we have developed a lower power, small, light-weight continuous wave (CW) laser spectrometer that can be utilized for highly sensitive scattering, fluorescence and Raman measurements. The capability exists of exciting and detecting fluorescence from aerosols in our ringdown cavity. We have found that it is possible to discriminate between biological and non-biological aerosols based on their fluorescence and/or Raman spectra. A shorter excitation wavelength, will normally be absorbed by bioaerosols more efficiently (compared to organic molecules) and thus produce stronger fluorescence signals.

By way of example as shown in FIG. 3, we can determine extinction coefficient, absorption and fluorescence using a single, commercially available solid-state continuous wave (CW) 976 nm pump laser. Because the 976 nm pump laser frequency can be doubled twice to produce both 488 nm (blue visible) and also 244 nm (UV) light using known frequency doubling techniques, (e.g., wave guides or nonlinear crystals) we can use this single 976 nm laser to excite the fluorescence of bioaersols with 488 nm blue and/or 244 nm UV light. Raman scattering can also be stimulated by the 488 nm light. Alternatively, as shown in FIG. 4, our cavity design permits the use of several independent CW lasers (4.1, 4.2 and 4.3) of different wavelengths emitting into the cavity simultaneously through different input mirrors It is not practical to measure Rayleigh scattering, bioaerosol fluorescence and Raman scattering using a single fixed wavelength laser. Also, as previously indicated, use of a single wavelength laser precludes obtaining meaningful particle size distribution information.

As indicated and shown in FIGS. 3, 4, 5 and 8, our cavity ringdown cell preferably uses a four mirror bowtie cavity configuration. This configuration provides a number of advantages. First is ease of alignment. If desired, the four mirrors allows for one, two or three input and likewise one, two or three output mirrors. Therefore, no pre-cavity beam combining optics are required, which greatly facilitates cavity alignment. Secondly, this configuration inherently results in twice the optical path length compared to a similarly dimensioned three mirror ring cavity. Finally, as previously indicated, this configuration can use four identical plano-concave mirrors, thus only one mirror coating run is required. This results in a meaningful cost saving in instrument production.

In one embodiment of this instrument, as shown in FIG. 4, it contains a triple wavelength, four mirror ringdown cavity filled by light from, for example, a 1.55 μm infrared distributed feedback (DFB) diode laser, a 675 nm visible Fabry-Perot (FP) diode laser and a 275 nm frequency tripled Ti:sapphire (UV) laser. A Nd:YAG pumped dye laser (red) can, if desired, be substituted for the Fabry-Perot laser. A frequency doubled diode laser can be used to provide light at 830 nm (near IR) and 415 nm (visible). Our instrument is capable of measuring both extinction and scattering at 675 nm using a photomultiplier tube. The measurement of both scatter and extinction at 675 nm enables determination of the single scatter albedo, Ω, at this wavelength in accordance with the formula below where $\sigma_{scat}$ is the scattering coefficient and $\sigma_{abs}$ is the absorption coefficient:

$$\Omega = \frac{\sigma_{scat}}{\sigma_{scat} + \sigma_{abs}}$$

The single scatter albedo is an important parameter which indicates atmospheric visibility.

In the embodiment illustrated in FIG. 3, the visible laser source consists of a fixed frequency diode laser emitting at 976 nm (near IR). Use of two doubling crystals allows for the generation of both 244 nm (UV) and also 488 nm (blue visible) light. Suitable detectors for the ringdown measurements are, by way of example, an InGaAs or Germanium amplified photodetector for the 976 nm channel and silicon photodiodes with a high gain preamplifier for the 244 nm and 488 nm signals. Scattered photons and fluorescence emission can be monitored using appropriate detectors placed above the ringdown cell axis as shown in FIG. 5. Blue photons (488 nm) scattered by particles in the beam path during the ringdown event can be collected and monitored using, for example, a photomultiplier tube (PMT) module. Scattered IR photons (976 nm) can be measured using an avalanche photodiode together with a 976 nm narrow bandpass filter to remove any longer wavelength fluorescence. Fluorescence signals are collected and monitored using a PMT module and appropriate notch filters to remove the 244, 488 and 976 nm radiation. Fluorescence can also be measured using a diffraction grating and CCD (charge couple device) array detector for complete fluorescence spectrum acquisition. Ringdown, scattering, Raman and fluorescence data are all acquired simultaneously. The measured ringdowns are analyzed and the extinction coefficients can be calculated using, for example, Windows based software. As shown in both FIGS. 3 and 4, a series of high reflectivity planar mirrors(3.8 and 3.9 in FIG. 3, and 4.4 through 4.9 in FIG. 4) are used to direct the output from the source laser or lasers into the ringdown cavity. If it is important to analyse the absorption features of one or more aerosol components, a tunable input laser capable of being tuned over the wavelength range of interest can be used in lieu of individual fixed frequency lasers or a frequency doubled laser. Optical parametric oscillator (OPO) lasers are suitable where tunability is desired.

Using either multiple input lasers, or frequency doubling of a single laser, our four mirror bow tie CRDS instrument shows a number of unique advantages:

Ultra-high extinction sensitivity. Our instrument has the ability to measure the extinction coefficient of an aerosol with a sensitivity up to $10^{-11}$ cm$^{-1}$ Hz$^{-1/2}$.

Ultra-high scattering sensitivity. By using high reflectivity mirrors, (e.g., >99%) there is a significant buildup of the optical intensity inside the cavity. This enhances its sensitivity to scattered light. The sensitivity of our instrument to scattered light is at least equal to that of the most advanced particle counting detectors.

Figure 6:
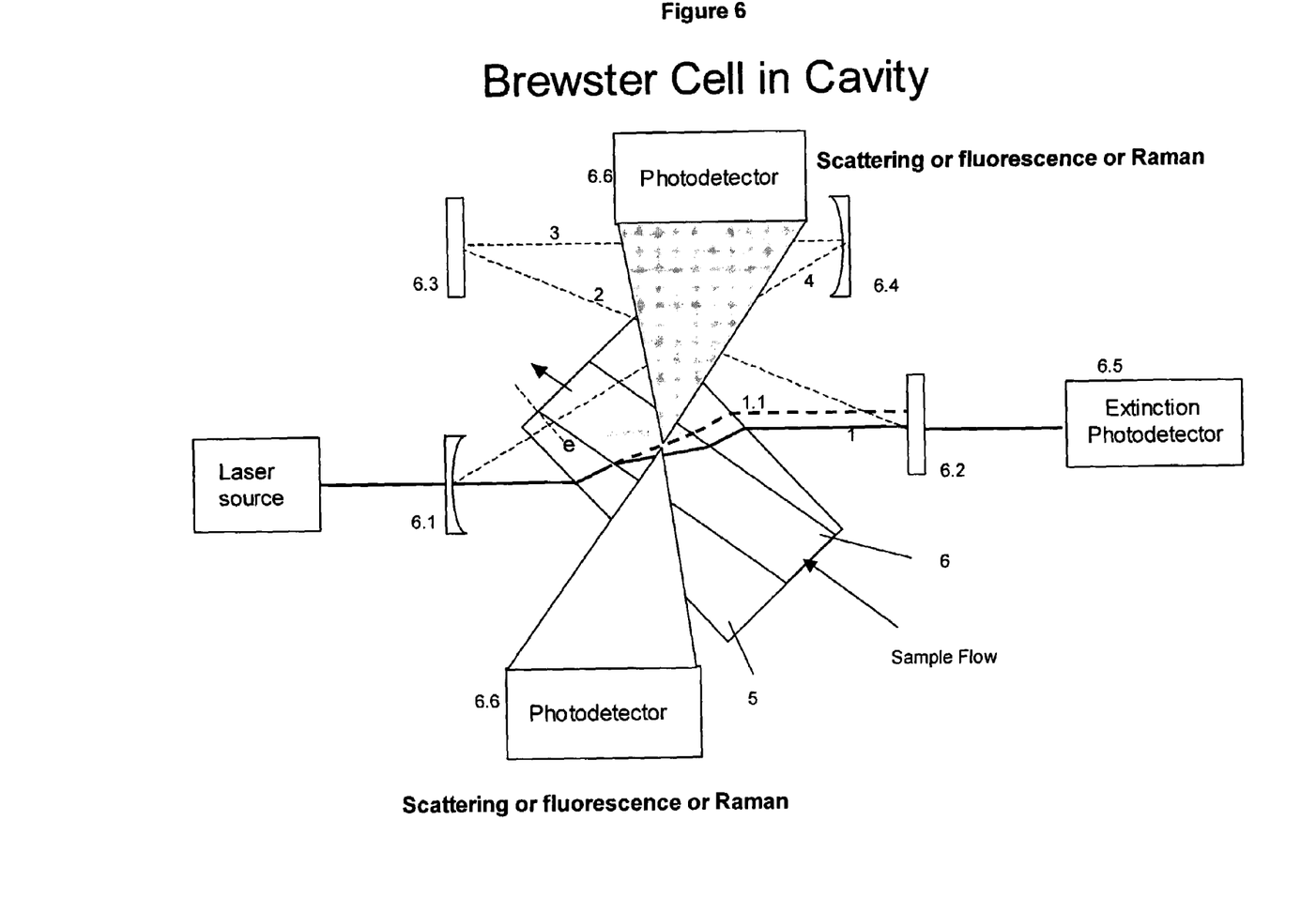
FIG. 6 shows a cavity design according to the present invention utilizing a Brewster cell to contain a liquid sample or a "dirty" sample which could contaminate the cavity mirrors.
Figure 7:
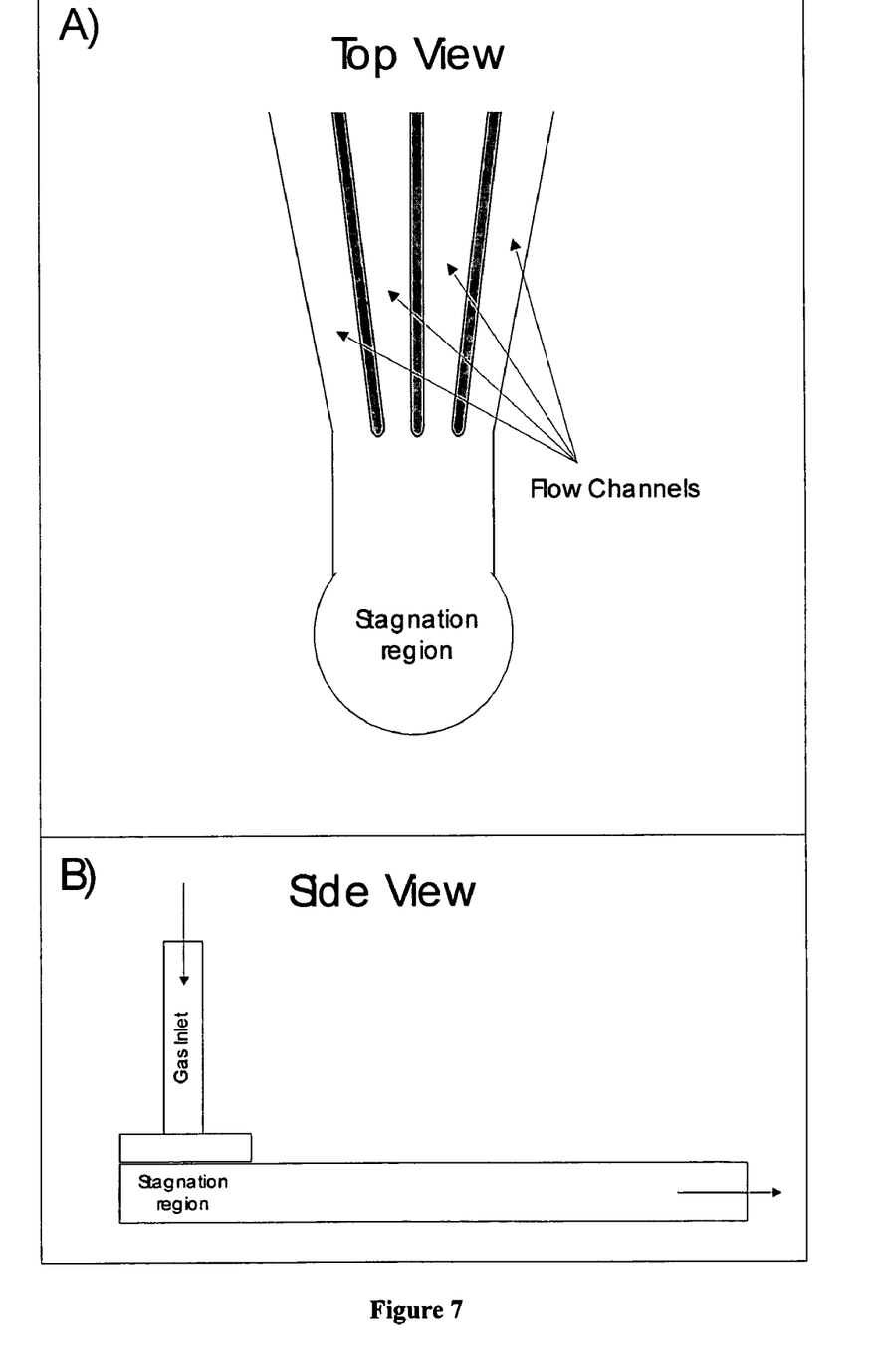
FIGS. 7a and 7b show a preferred design for the sample gas inlet system.

High fluorescence sensitivity. Particularly with our bow tie ringdown cavity, the UV light which is preferably used for exciting fluorescence can build up by a factor of 100 to 1000 thereby providing intracavity power levels exceeding 1 watt with only a few mW of incident laser light. Utilizing Brewster-cells within the cavity as shown in FIG. 6, the sample can be confined to a small volume to further increase signal strength. Alternatively in lieu of UV light, fluorescence can be induced by visible light (preferably in the 400–500 nm range). Therefore, at least one of the laser beams used in the present invention should provide light with a wavelength in the range of 100–500 nm. Our instrument can measure aerosols with particle sizes ranging from 0.5 to 100 microns. It has an accuracy and precision of 1% for aerosols with an extinction coefficient greater than $10^{-5}$ m$^{-1}$, with a 1 second integration time.

Self-calibrating operation. Since CRDS is inherently self-calibrating, our instrument requires no test samples or consumables.

Inherent robustness. In CRDS, the measurement of the extinction coefficient depends only on the rate of decay of light inside the cavity. The measurement is therefore insensitive to laser intensity fluctuations.

Design flexibility. Our basic platform can be easily reconfigured to operate at a variety of different wavelengths and can incorporate multiple wavelengths and/or tunable lasers in one device. The instrument can be adapted to measure aerosols of varying particle size and provide information about their size distribution Since the instrument measures the fluorescence emission from fluorophores interacting with the intracavity laser radiation it is highly advantageous that the optical intensities which build-up inside our high finesse cavity are able to generate high levels of detectable fluorescence necessary to permit aerosol particle type discrimination.

Detectors

Figure 8:
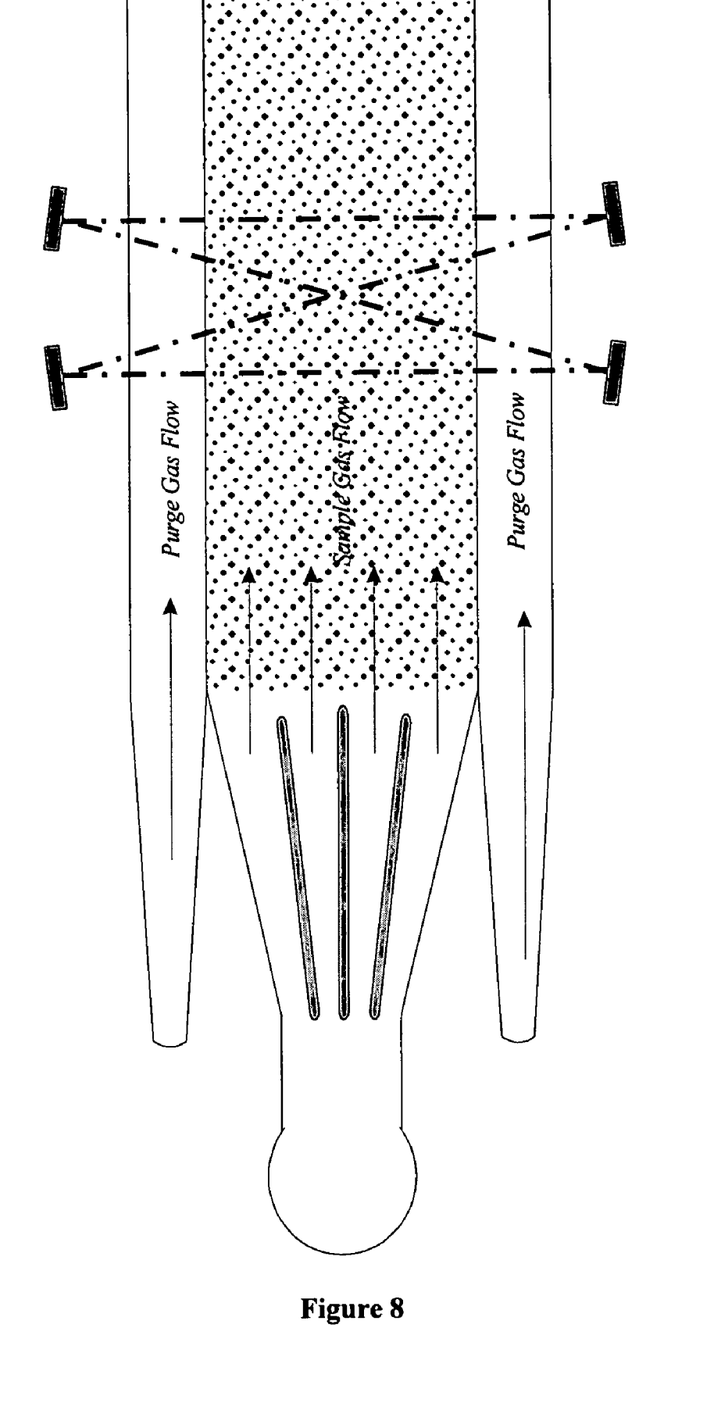
FIG. 8 is a schematic which illustrates the flow pattern for the sample gas and also for the purge gas which helps to maintain the mirror surfaces clean and highly reflective when using our preferred gas inlet system.

Extinction, fluorescence and Rayleigh scattering can be measured using known types of detectors such as avalanche photo-diode or photo multiplier tube (PMT) detectors coupled with appropriate collection lenses positioned as shown in FIG. 5. Charge couple device (CCD) arrays are particularly useful for Raman detection. Scattered photons and fluorescence emission can be monitored using appropriate detectors placed above the ringdown beam path. As seen in FIG. 5, the preferred detection system comprises a plurality of forward/back Rayleigh scattering collection lenses (5.2) and also fluorescence (and/or Rayleigh and Raman scattering) collection lenses (5.3) place above and advantageously also below the beam path (5.4) and the cavity mirrors (5.1). Band pass filters are advantageously positioned between each collection lens and its corresponding detector to remove (block) extraneous frequencies. For example, the detector used for measuring fluorescence should have a filter which blocks the emission frequencies of the laser. It is important to note that fluorescence and Rayleigh scattering detection normally requires at least one different set comprising a collection lens, filter and detector. However, it is possible to use a single unit comprising a collection lens, detector and a tunable filter to detect both fluorescence and Rayleigh scattering. Raman scattering is preferably detected using a dispersive element (e.g., a diffraction grating) and a CCD array detector. As sample flow traverses the ringdown cell, transverse (perpendicular) to the optical axis, as shown in FIG. 8, photons scattered by particulate matter are collected using a multi-unit optical collection system placed above (and/or below) the central portion of the ringdown cell as seen in FIG. 5. An objective lens is employed to collect photons emitted within the field of view of the objective lens. Photons scattered by particles within this viewing region are collected by the lenses and relayed to an appropriate detector. Although a single (or multiple) scattering detector(s) located above the beam intersection point (indicated as 3.0, 4.0 and 5.2 and 5.3 in FIGS. 3, 4 and 5, respectively, can be used, the use of multiple detectors to measure both foreword and back scattering is advantageous as a comparison of forward and back scattering provides a basis for conclusions about the shape of the aerosol particles. Suitable bandpass filters are used to remove interfering fluorescence emission resulting from the visible or UV excitation. An identical collection system can be used for fluorescence detection. In this case, appropriate band pass filters can be used to remove scattered photons. Fluorescence emission as well as Rayleigh scattered 488 nm photons can be monitored using, for example, a photomultiplier tube (PMT) module, while scattered IR photons are preferably measured using a large area avalanche photodiode. A diffraction grating and CCD array detector can be incorporated to provide complete spectral acquisition in real-time.

Brewster Cell

As shown in FIG. 6, our instrument can be adapted when it is sometimes necessary to perform measurements on a liquid sample or a highly contaminated gaseous sample The adaption consists of containing the sample within a Brewster cell present within the optical cavity. A detailed explanation of the use of a Brewster cell in connection with CRDS or ICOS is set forth in co-pending, commonly assigned U.S. patent application Ser. No. 10/700947, filed Nov. 31, 2003, the teaching of which is incorporated herein by this reference. As indicated, cavity enhanced optical detection can be used for liquid, aerosol, or gaseous samples. For gaseous samples, intracavity interfaces are typically not present, so there are no corresponding interface reflection losses to contribute to round trip parasitic loss. However, intracavity interfaces are typically present for aerosol or liquid samples. For example, contamination of the mirror surfaces by aerosols can create problems so that these samples are advantageously enclosed in an intracavity cell. This cell will create interfaces (e.g., windows) within the optical resonator. Likewise, for a liquid sample contained in a flow cell present within a cavity, the interfaces between the liquid and the inner wall of the flow cell as well as the exterior wall surfaces of the flow cell are all intracavity interfaces. U.S. Pat. No. 6,452,680 teaches the minimization of intracavity reflection loss when examining solid or liquid samples by positioning the sample such that optical radiation circulating within the optical resonator is, insofar as possible, incident on the sample-induced interfaces at an angle approximating Brewster's angle and is p-polarized relative to these interfaces. Since reflection is minimized for p-polarized incidence on an interface at Brewster's angle, this arrangement significantly reduces reflection-induced parasitic loss. FIG. 6 is a schematic illustration of this cell configuration. In this design the liquid flow channel is tilted within the cell so that the light beam strikes each surface at the correct Brewster's angle for the specific interface (e.g. air→fused silica→liquid or gaseous sample→fused silica→air). With the appropriate polarization of light, the interface reflections are minimized, thereby allowing the light to pass back and forth through the cell multiple times, resulting in a relatively long ring-down constant. In the example shown in FIG. 1b, using a fused silica cell and water as the sample liquid, angle e is 7.9° and angle a is 55.6° so that the light refracts through the cell, hitting each interface surface at approximately Brewster's angle for minimum reflection. In FIG. 6 solid line 1 indicates the light path through flow cell 5 including flow channel 6 containing the analyte sample. Dashed line 1.1 shows the altered light path if the refractive index of the analyte changes. Note that mirrors 6.2 and 6.3 are planar so that light path 2 is not affected by the change in refractive index. Mirrors 6.1 and 6.4 will preferably be plano-concave as shown. Note that light paths 2, 3 and 4 are shown as dotted lines since the flow cell is out of the plane of these lights paths and only is intersected by beam path1 (or 1.1). Extinction is measured by detector 6.5. Photodetectors 6.6, which are also out of the plane of the beam path, are meant to represent multiple detectors, as previously described, to measure Rayleigh scattering, Raman scattering and fluorescence.

Air Flow

A preferred sample handling system consists of a stagnation region which the sample gas enters vertically and then exits into the cavity via horizontal flow channels. This sample inlet design, as shown in FIGS. 7a, 7b and 8, results in a laminar flow of the sample gas transverse (perpendicular) to the ringdown cavity optical axis. As shown, the illustrated sample handling system injects a laminar sample flow into the ringdown cavity and also provides a protective purge gas (e.g., dry, filtered air or nitrogen) flow on both sides of the sample region between the cavity mirrors and the sample. Without use of the stagnation region and the vertical entry of the sample gas into the stagnation region it is sometimes difficult to achieve the laminar sample flow which greatly facilitates accurate sample analysis.

Detecting Fluorescence in the Ringdown Cavity

Fluorescence spectroscopy is an ideal extension of CRDS due to the inherent intracavity power build-up of high-finesse optical cavities. The intracavity power can be estimated by:

$$I_{intracavity} = \frac{P_c \xi}{T}$$

where $P_c$ is the power coupled into the cavity mode being observed, $\xi$, is the injection efficiency (which is a function of cavity length scanning frequency), and T is the cavity transmission. For example, a suitable laser can readily produce 20 mW of power at 488 nm e.g., an argon ion laser. For a 1 kHz scanning frequency, the intracavity power will be approximately 1 watt. For a slower scanning frequency of 100 Hz, the intracavity power will be approximately 9 watts. Given a mode size of 0.25 mm, the intracavity power density is on the order of 500 watts/cm$^2$ for a 1 kHz scanning frequency. These power densities are equal to those found in commercial flow cytometers. The incident power captured by a 1 μm diameter particle will be approximately 4 μW. By way of example, for a 1 μm diameter fluorescein coated polystyrene sphere, assuming a molar extinction coefficient of 90,000 M$^{-1}$ cm$^{-1}$, a single particle will absorb approximately 30% of the incident light. With the intracavity power estimated above, this leads to the generation of approximately 1 μW of fluorescence emission per particle.

To determine the amount of light that will be captured by the fluorescence detector, one first needs to calculate the amount of emitted fluorescence that can be collected. For example, if one uses a 0.17 NA (numerical aperture) lens with a magnification of 0.1, the viewing volume is 0.16 cm$^3$. For a particle concentration of 100 per cm$^3$, there will be 3.2 particles in the viewing region during each ringdown event if the collection lens is placed in the center of the ringdown cell.

With a system viewing angle of 6 degrees, the corresponding solid angle is:

$$\Omega = 4\pi \sin\left(\frac{\theta}{4}\right)^2$$

or $\Omega = 8.6 \times 10^{-3}$ steradians. The fraction of power collected by the optical system will be $\Omega/4\pi$ or approximately $7 \times 10^{-4}$. Thus the total power incident onto the detector will be approximately 0.7 nW. For a PMT with a sensitivity of 80 mA/watt, a gain of $1 \times 10^5$, and a load resistance of 1 MΩ, this system should produce about 5.6 V of signal per particle. The voltage noise of the PMT under these conditions is less than 1 mV, which will result in a very high signal to noise (S/N) ratio. Our system permits measurement of both the total laser induced fluorescence and also the fluorescent spectrum at the incident wavelength which significantly enhances the discrimination between biological and non-biological aerosols.

The invention claimed is:

1. A cavity enhanced optical detector comprising:
   i) a source of CW laser light;
   ii) a high finesse resonant cavity comprising at least three spaced apart, high-reflectivity mirrors, to receive light from the laser light source;
   iii) at least one photo-detector for measuring an extinction coefficient of an analyte that is positioned in the resonant cavity; and
   iv) at least a second photo-detector for measuring intensity of fluorescence emission from the analyte.

2. A cavity enhanced optical detector in accordance with claim 1, further comprising at least a third photo-detector for measuring a light scattering coefficient of said analyte.

3. A cavity enhanced optical detector in accordance with claim 1, wherein said resonant cavity comprises four mirrors in a bow-tie configuration.

4. A cavity enhanced optical detector in accordance with claim 3, wherein a first and second of said mirrors are planar and a third and fourth of said mirrors are plano-concave.

5. A cavity enhanced optical detector in accordance with claim 3, wherein all four of said mirrors are plano-concave.

6. A cavity enhanced optical detector in accordance with claim 1, configured as a cavity ring-down spectrometer.

7. A cavity enhanced optical detector in accordance with claim 1, wherein said extinction coefficient and said intensity of said analyte are measured substantially simultaneously.

8. A cavity enhanced optical detector in accordance with claim 1, further comprising detection means for measuring Raman scattering by said analyte of light provided by said source.

9. A cavity enhanced optical detector in accordance with claim 8, wherein said detection means comprises a CCD array.

10. A cavity enhanced optical detector in accordance with claim 1, wherein said analyte is contained in a container having a volume smaller than a volume of said cavity.

11. A cavity enhanced optical detector in accordance with claim 10, wherein said container is a Brewster Cell.

12. A cavity enhanced optical detector in accordance with claim 1, wherein said at least one detector for measuring said extinction coefficient is a photo-diode.

13. A cavity enhanced optical detector in accordance with claim 1, wherein said detector for measuring said intensity of said fluorescence emission is at least one of a photo multiplier tube and an avalanche photo-diode.

14. A cavity enhanced optical detector in accordance with claim 2, wherein said detector for measuring said scattering coefficient is at least one of a photo multiplier tube and an avalanche photo-diode.

15. A cavity enhanced optical detector in accordance with claim 2, wherein said at least one detector for measuring said fluorescence emission is a first plurality of detectors, and said at least said third detector for measuring said scattering coefficient is a second plurality of detectors.

16. A cavity enhanced optical detector in accordance with claim 2, wherein said at least said third detector for measuring said scattering coefficient of said analyte is a plurality of detectors, wherein at least a first of the plurality of the detectors is positioned to measure forward scattering and at least a second of the plurality of detectors is positioned to measure back scattering.

17. A cavity enhanced optical detector in accordance with claim 1, wherein said photo-detector for measuring said intensity of said fluorescence emission further comprises a fixed frequency filter.

18. A cavity enhanced optical detector in accordance with claim 1, wherein said photo-detector for measuring said intensity of said fluorescence emission further comprises a filter having a pass frequency that can be varied.

19. A cavity enhanced optical detector in accordance with claim 1, further comprising a dispersive element and detector array for measuring said intensity of said fluorescence emission.

20. A cavity enhanced optical detector comprising:
   i) a source of CW laser light;
   ii) a high finesse resonant cavity comprising at least three spaced apart, high-reflectivity mirrors, to receive light from the laser light source;
   iii) at least one photo-detector for measuring an extinction coefficient of an analyte that is positioned in the resonant cavity;
   iv) at least a second photo-detector for measuring intensity of Raman scattering from the analyte.

* * * * *